United States Patent [19]

Itoh et al.

[11] Patent Number: 4,758,656

[45] Date of Patent: Jul. 19, 1988

[54] NOVEL HUMAN INTERFERON-GAMMA POLYPEPTIDE DERIVATIVE

[75] Inventors: Seiga Itoh, Sagamihara; Susumu Sekine, Machida; Akiko Saito, Machida; Moriyuki Sato, Machida, all of Japan

[73] Assignee: Kyowa Hakko Kogyo Co., Ltd., Tokyo, Japan

[21] Appl. No.: 683,363

[22] Filed: Dec. 19, 1984

[30] Foreign Application Priority Data

Dec. 26, 1983 [JP] Japan .............................. 58-246456
Jul. 25, 1984 [JP] Japan .............................. 59-154713

[51] Int. Cl.$^4$ .................. C07K 13/00; C07K 15/26; C12P 21/00; A61K 45/02
[52] U.S. Cl. .................................. 530/351; 424/85; 435/68; 435/811; 435/320
[58] Field of Search ............... 530/351; 435/68, 811; 424/85

[56] References Cited

U.S. PATENT DOCUMENTS 4,457,867 7/1984 Ishida ................................ 530/351
4,604,284 8/1986 Kung et al. ........................ 530/351

FOREIGN PATENT DOCUMENTS

| | | |
|---|---|---|
| 0083777 | 7/1983 | European Pat. Off. . |
| 0089676 | 9/1983 | European Pat. Off. . |
| 0103898 | 3/1984 | European Pat. Off. . |
| 0112976 | 7/1984 | European Pat. Off. . |
| 0128467 | 12/1984 | European Pat. Off. . |
| 0136620 | 4/1985 | European Pat. Off. . |
| 0145174 | 6/1985 | European Pat. Off. . |
| 0146354 | 6/1985 | European Pat. Off. . |
| 0146413 | 6/1985 | European Pat. Off. . |
| 0147175 | 7/1985 | European Pat. Off. . |
| 83/04053 | 11/1983 | PCT Int'l Appl. . |

OTHER PUBLICATIONS

Devos et al., Nucleic Acid Research, vol. 10, pp. 2487–2500, 1982.
Gray et al., Nature, vol. 295, pp. 503–508, 1982.
Shepard et al., Nature, vol. 294, pp. 563–565, 1981.

*Primary Examiner*—Blondel Hazel
*Attorney, Agent, or Firm*—Fitzpatrick, Cella, Harper & Scinto

[57] ABSTRACT

Disclosed is a novel derivative of human interferon-$\gamma$ polypeptide, a recombinant plasmid wherein a DNA fragment coding for said polypeptide is incorporated and a process for producing the derivative of human interferon-$\gamma$ polypeptide using a microorganism containing said plasmid.

1 Claim, 7 Drawing Sheets

NOVEL HUMAN INTERFERON-GAMMA POLYPEPTIDE DERIVATIVE

BACKGROUND OF THE INVENTION

Interferons (referred to as IFN hereinafter) so far known can be classified into three large groups, i.e. IFN-α, IFN-β and IFN-γ. IFN-α is mainly produced from leukocytes, IFN-β from fibroblasts and IFN-γ from T-lymphocytes. These IFNs have been noted as biologically active substances having anti-virus activity, activating activities upon natural killer cells and macrophages, anti-tumor activity, and the like. However, the conventional methods for obtaining IFNs by isolation from leukocytes and cultured cells cannot provide them sufficiently.

Recombinant DNA technology has now been developed to the extent that the mass production of substances which are secreted only in a small amount in cells of higher animals and are hard to isolate such as IFN has become possible by using microorganisms. For example, mRNAs of IFN-β and IFN-α were respectively isolated from cells and DNA complementary to the mRNA (cDNA) was synthesized enzymatically and cloned in *Escherichia coli* [Taniguchi, et al.: Proc. Jap. Acad., 55 (B), 464–469 (1979), Nagata, et al.: Nature 284, 316–320 (1980)].

As for IFN-γ, there has been a report that it has a stronger cell-inhibiting activity than other IFNs based on the experiment using animal cells [B. Y. Rubin and S. L. Gupta: Proc. Natl. Acad. Sci., USA, 77, 5928–5932 (1980)]. Furthermore, cloning of an IFN-γ cDNA into *Escherichia coli* and determination of its base sequence were recently reported [P. W. Gray, et al.: Nature 295, 503 (1982), R. Devos, et al.: Nucleic Acids Research 10, 2487 (1982)].

The present inventors have independently cloned a DNA coding for IFN-γ to obtain a clone coding for a novel IFN-γ wherein, as apparent from the base sequence illustrated in Table 1, the ninth amino acid of the mature IFN-γ reported by Devos, et al., Lysine (Lys) (AAA), is replaced with glutamine (Gln) (CAA). Further, the IFN-γ gene was incorporated into vector pKYP-10 having tryptophan prompter (Japanese Published Unexamined Patent Application No. (110600/83) and mass production of the IFN-γ in *Escherichia coli* has been achieved.

Thereafter, the present inventors have studied the production of derivatives of IFN-γ polypeptide using the IFN-γ gene illustrated in Table 1 as a starting material.

It was reported that deletion of 11 amino acids from the C-terminal of IFN-α decreased specific activity to one-third [A. E. Franke, et al.: DNA 1, 223–230 (1982)], whereas addition of 18 amino acids to the N-terminal of IFN-α did not change specific activity [R. M. King, et al.: J. Gen. Virol. 64, 1815–1818 (1983)].

Derivatives of IFN-γ have not yet been reported. The present inventors have constructed a derivative wherein the third amino acid of IFN-γ illustrated in Table 1, cysteine (Cys) was replaced with tyrosine (Tyr) (referred to as 3-Tyr-IFN-γ hereinafter) and found that the specific activity was 2–4 times stronger than that of the parent IFN-γ. Further, the derivatives wherein the Cys at the position 1 was replaced with serine (Ser) (1-Ser-IFN-γ), the Cys at the position 3 was replaced with Ser (3-Ser-IFN-γ), the Cys at the positions 1 and 3 were replaced with Ser (1,3-Ser-IFN-γ) and N-terminal amino acids of IFN-γ illustrated in Table 1 were deleted were constructed. Equivalent or more interferon activity was detected for all the derivatives compared with the starting IFN-γ.

SUMMARY OF THE INVENTION

The present invention relates to a novel derivative of human interferon-γ polypeptide, a recombinant plasmid wherein a DNA fragment coding for said polypeptide is incorporated and a process for producing the derivative of human interferon-γ polypeptide using a microorganism containing said plasmid.

TABLE 1

CACATTGTTCTGATCATCTGAAGATCAGCTATTAGAAGAGAAAGATCAGTTAAGTCCTTTGG

ACCTGATCAGCTTGATACAAGAACTACTGATTTCAACTTCTTTGGCTTAATTCTCTCGGAAACG

```
      -20
 met  lys  tyr  thr  ser  tyr  ile  leu  ala  phe  gln  leu  cys  ile  val  leu  gly
 ATG  AAA  TAT  ACA  AGT  TAT  ATC  TTG  GCT  TTT  CAG  CTC  TGC  ATC  GTT  TTG  GGT 1                                         10
 ser  leu  gly  CYS  TYR  CYS  GLN  ASP  PRO  TYR  VAL  GLN  GLU  ALA  GLU  ASN  LEU
 TCT  CTT  GGC  TGT  TAC  TGC  CAG  GAC  CCA  TAT  GTA  CAA  GAA  GCA  GAA  AAC  CTT
                  1                                         ↑

20                                        30
 LYS  LYS  TYR  PHE  ASN  ALA  GLY  HIS  SER  ASP  VAL  ALA  ASP  ASN  GLY  THR  LEU
 AAG  AAA  TAT  TTT  AAT  GCA  GGT  CAT  TCA  GAT  GTA  GCG  GAT  AAT  GGA  ACT  CTT

40
 PHE  LEU  GLY  ILE  LEU  LYS  ASN  TRP  LYS  GLU  GLU  SER  ASP  ARG  LYS  ILE  MET
 TTC  TTA  GGC  ATT  TTG  AAG  AAT  TGG  AAA  GAG  GAG  AGT  GAC  AGA  AAA  ATA  ATG 50                                        60
 GLN  SER  GLN  ILE  VAL  SER  PHE  TYR  PHE  LYS  LEU  PHE  LYS  ASN  PHE  LYS  ASP
 CAG  AGC  CAA  ATT  GTC  TCC  TTT  TAC  TTC  AAA  CTT  TTT  AAA  AAC  TTT  AAA  GAT
```

TABLE 1-continued

```
                        70                              80
ASP GLN SER ILE GLN LYS SER VAL GLU THR ILE LYS GLU ASP MET ASN VAL
GAC CAG AGC ATC CAA AAG AGT GTG GAG ACC ATC AAG GAA GAC ATG AAT GTC

90
LYS PHE PHE ASN SER ASN LYS LYS LYS ARG ASP ASP PHE GLU LYS LEU THR
AAG TTT TTC AAT AGC AAC AAA AAG AAA CGA GAT GAC TTC GAA AAG CTG ACT 100                                         110
ASN TYR SER VAL THR ASP LEU ASN VAL GLN ARG LYS ALA ILE HIS GLU LEU
AAT TAT TCG GTA ACT GAC TTG AAT GTC CAA CGC AAA GCA ATA CAT GAA CTC 120                                     130
ILE GLN VAL MET ALA GLU LEU SER PRO ALA ALA LYS THR GLY LYS ARG LYS
ATC CAA GTG ATG GCT GAA CTG TCG CCA GCA GCT AAA ACA GGG AAG CGA AAA 140                    146
ARG SER GLN MET LEU PHE [ARG] GLY ARG ARG ALA SER GLN
AGG AGT CAG ATG CTG TTT [CGA] GGT CGA AGA GCA TCC CAG TAA TGGTTGTCCTG
                         (↑)
```

CCTGCAATATTTGAATTTTAAATCTAAATCTATTTATTAATATTTAACATTATTTATATGGGGAATATATTTTTAG

ACTCATCAATCAAATAAGTATTTATAATAGCAACTTTTGTGTAATGAAAATGAATATCTATTAATATATGTATTA

TTTATAATTCCTATATCCTGTGACTGTCTCACTTAATCCTTTGTTTTCTGACTAATTAGGCAAGGCTATGTGATT

ACAAGGCTTTATCTCAGGGGCCAACTAGGCAGCCAACCTAAGCAAGATCCCATGGGTTGTGTGTTTATTTCACTT

GATGATACAATGAACACTTATAAGTGAAGTGATACTATCCAGTTACTACCCCCCC ...
                                              ↑

DETAILED DESCRIPTION OF THE INVENTION

An object of the present invention is to provide a recombinant plasmid wherein a DNA coding for a novel derivative of human IFN-γ is incorporated, a microorganism containing the plasmid, a process for producing a novel derivative of human IFN-γ polypeptide using the microorganism and the derivative of human IFN-γ polypeptide per se.

Construction of the recombinant plasmid is carried out using cDNA obtained from messenger RNA coding for IFN-γ by recombinant DNA technology or chromosomal DNA coding for IFN-γ as a starting material.

In the present invention, any human IFN-γ cDNA are employable and pIFN-γ-G4 is preferably used. Escherichia coli containing pIFNγ-G4 has been deposited with the American Type Culture Collection, USA under accession number ATCC 39123.

The base sequence of the IFN-γ DNA in pIFNγ-G4 was determined by the method of Maxam and Gilbert [Proc. Natl. Acad. Sci. 74, 560 (1977)] and is illustrated in Table 1.

Comparison of the human IFN-γ cDNA in pIFNγ-G4 and the known IFN-γ cDNA [R. Devos, et al.: Nucleic Acids Research, 10, 2487 (1982)] reveals the following. The first base [adenine (A)] of the triplet coding for lysine (the ninth amino acid of the mature human IFN-γ polypeptide) in the known IFN-γ is replaced by cytosine (C) in the pIFNγ-G4 cDNA. Accordingly, the ninth amino acid from the N-terminal of the human IFN-γ polypeptide encoded by the pIFNγ-G4 cDNA is glutamine, and not lysine. Therefore, it is apparent that pIFNγ-G4 codes for a novel human IFN-γ polypeptide.

Derivatives of IFN-65 obtained by deletion or replacement of amino acids of IFN-γ illustrated in Table 1 are also novel IFN-γ derivatives.

As the plasmid to incorporate a DNA coding for IFN-γ derivative, any plasmid can be used so long as the DNA incorporated therein can be expressed in Escherichia coli. Preferably, a plasmid wherein a foreign DNA can be inserted downstream from a suitable promoter such as trp promoter or lac promoter and the length between Shine-Dalgarno sequence (referred to as SD sequence hereinafter) and initiation codon (ATG) is adjusted, for example, to 6-18 base pairs is employed. Preferred examples are pKYP10, pKYP11 and pKYP12 which were constructed by the present inventors (Japanese Published Unexamined Patent Application No. 110600/83).

Figure 1:
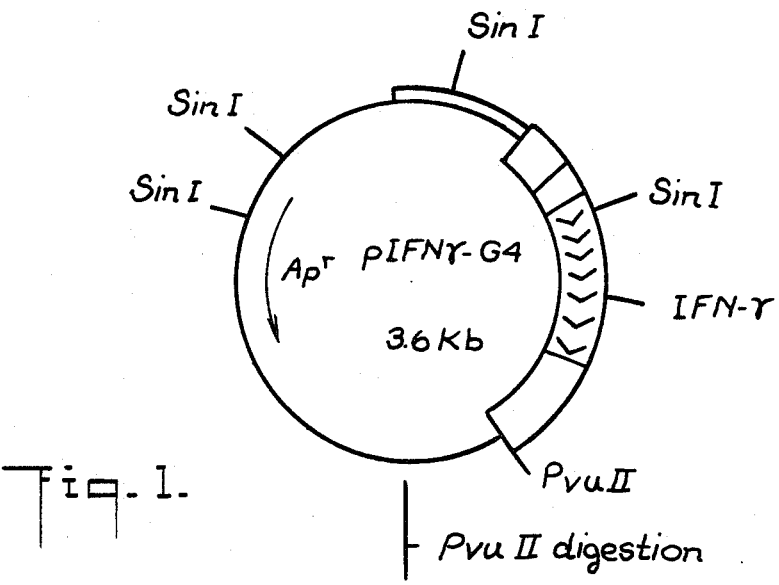
FIG. 1 is the flow sheet for construction pGBD-1.
Figure 1:
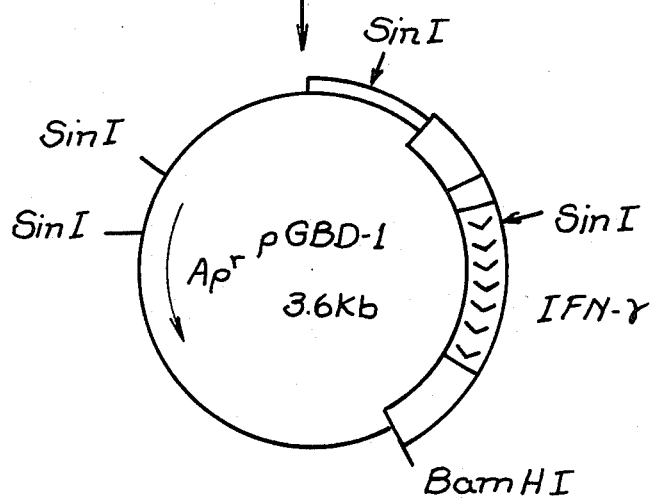

As illustrated in FIG. 1, pIFNγ-G4 is cleaved with PvuII and BamHI linker is introduced into the cleavage site to obtain pGBD-1.

Figure 2:
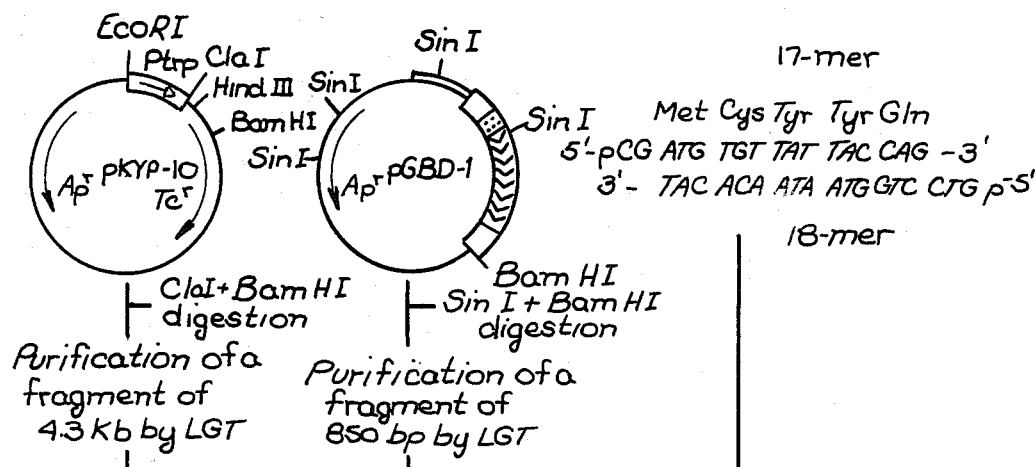
FIG. 2 is the flow sheet for constructing pGSB-6 and pGVA-4.
Figure 2:
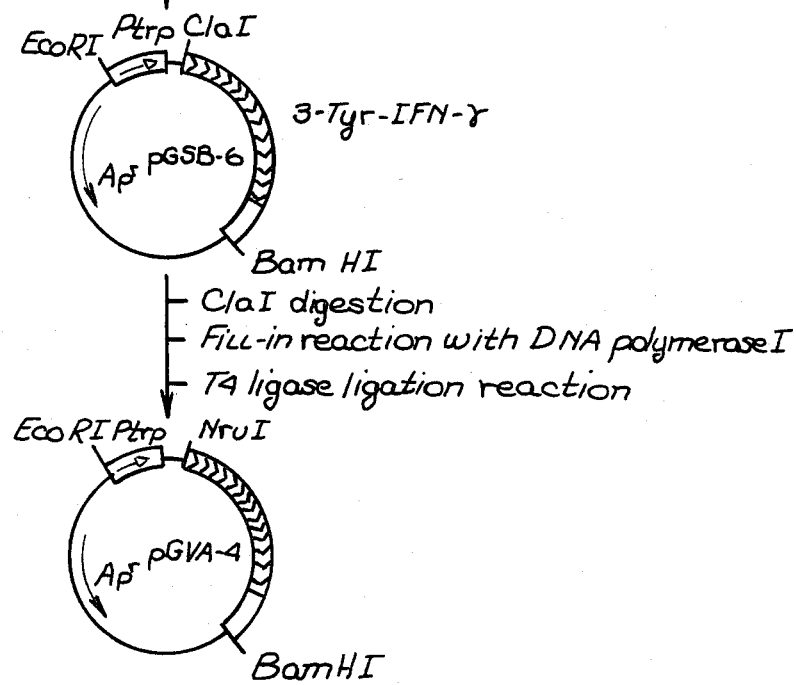
Figure 3:
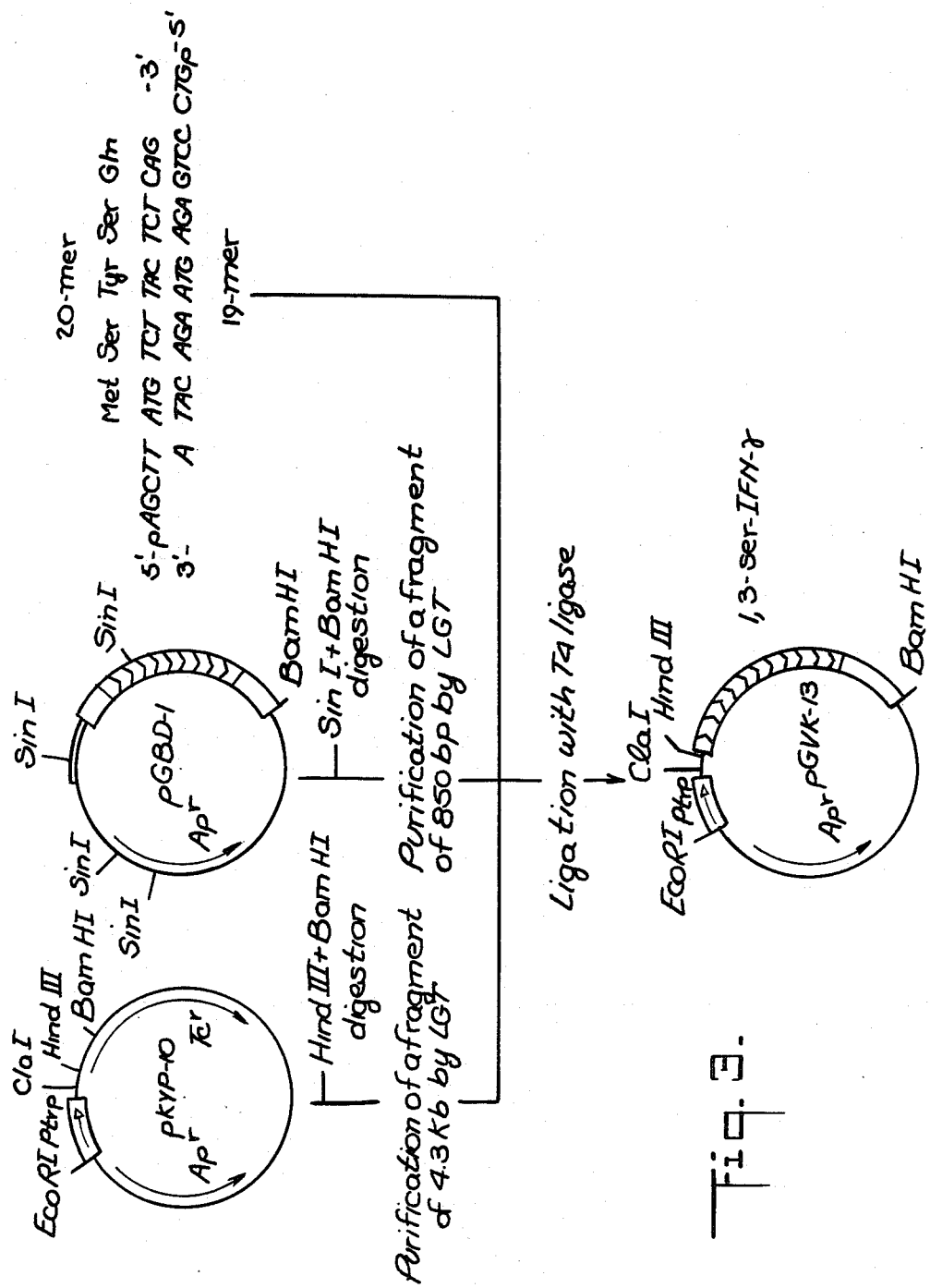
FIG. 3 is the flow sheet for constructing pGVK-13.

Then, pGBD-1 is digested with SinI and BamHI and a fragment of about 850 bp is purified by low-gellingtemperature agarose gel electrophoresis (LGT method) [L. Wieslander: Analytical Biochemistry 98, 305 (1979)]. pKYP-10 is digested with ClaI and BamHI and a fragment of about 4.3 kb is purified. The thus obtained DNA fragments and a synthetic DNA illustrated in FIG. 2 which codes for Tyr as the third amino acid are ligated with T4 DNA ligase to obtain pGSB-6. Then, pGSB-6 is digested with ClaI and subjected to fill-in reaction with DNA polymerase I and ligation reaction with T4 DNA ligase to obtain pGVA-4. The same procedure is repeated except for using the synthetic DNA illustrated in FIG. 3 which codes for Ser as the first and third amino acids to obtain plasmid pGVK-13 which codes for a derivative wherein the N-terminal first and third amino acids of IFN-γ, Cys, are replaced with Ser.

Figure 4:
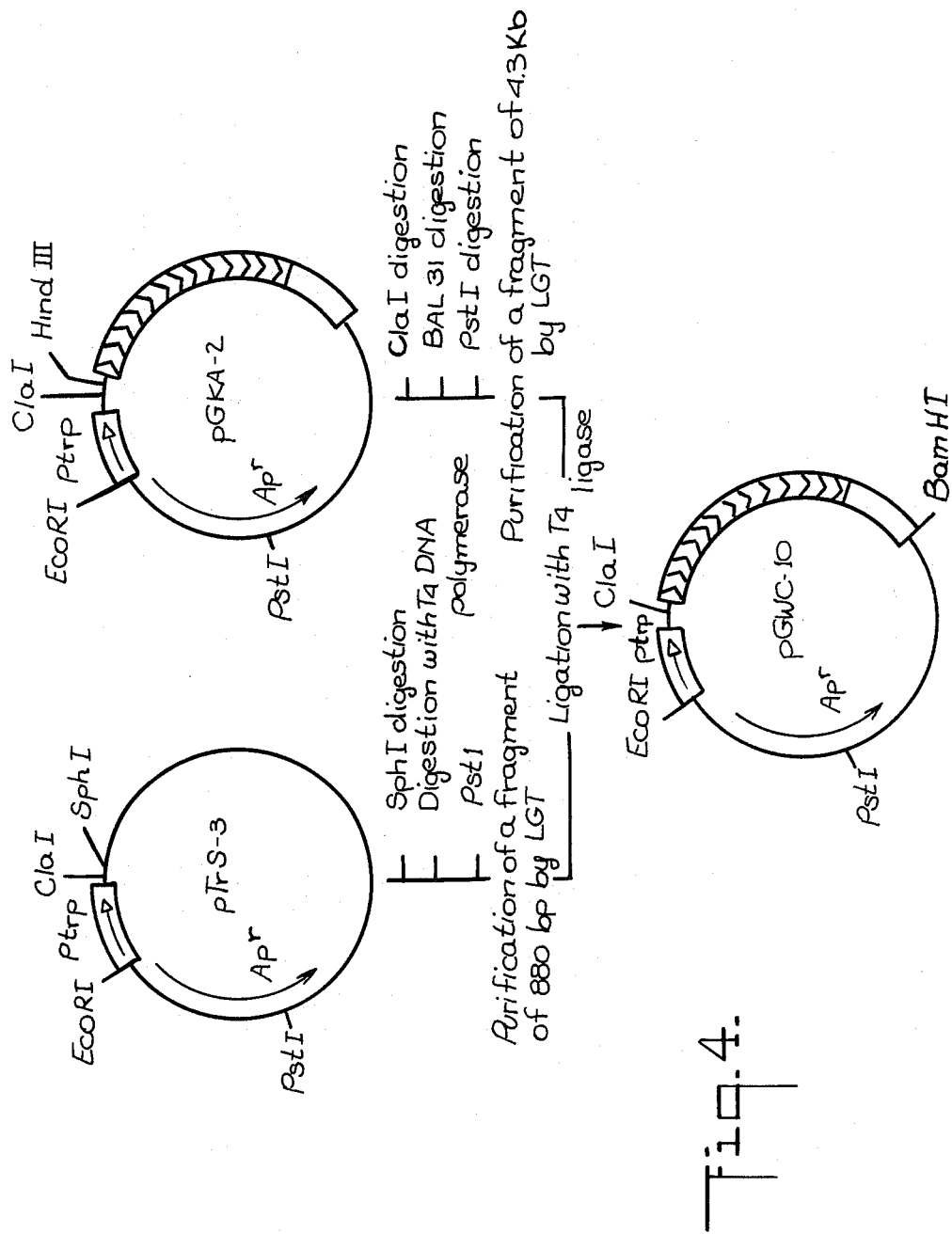
FIG. 4 is the flow sheet for constructing pGWC-10.

In order to obtain IFN-γ derivative wherein N-terminal amino acids are deleted, as illustrated in FIG. 4, pGKA-2 is digested with ClaI, treated with Bal31 for a short period of 1–30 minutes to cut out the DNA coding for N-terminal amino acid of IFN-γ and digested with PstI and a fragment of 4.3 Kb is purified. Separately, vector pTrS-3 containing initiation codon is digested with SphI, treated with DNA polymerase I and digested with PstI and a fragment of 880 bp is purified. Both fragments are ligated with T4 ligase to obtain pGWC-10.

Reaction conditions required for the recombinant DNA technology described above are generally as follows.

Digestion of the DNA with restriction enzymes is usually carried out by reacting 0.1 to 20 μg of DNA with 0.1–100 units, preferably 1–3 units of restriction enzyme per 1 μg of DNA in a mixture of 2–200 mM, preferably 10–40 mM Tris-HCl (pH 6.0–9.5, preferably pH 7.0–8.0), 0–200 mM NaCl and 2–20 mM, preferably 5–10 mM MgCl$_2$ at 20°–70° C. (optimal temperature depends on restriction enzymes used) for 15 minutes to 24 hours. Reaction is usually stopped by heating at 55°–75° C. for 5–30 minutes, or alternatively by inactivating the restriction enzyme with the reagent such as phenol or diethylpyrocarbonate.

Purification of the DNA fragments formed by digestion with restriction enzymes is carried out by LGT method or polyacrylamide gel electrophoresis [A. M. Maxam, et al.: Proc. Natl. Acad. Sci., USA 74, 560 (1977)].

Ligation of the DNA fragments is carried out with 0.3–10 units of T4 DNA ligase in a mixture of 2–200 mM, preferably 10–40 mM Tris-HCl (pH 6.1–9.5, preferably 7.0–8.0), 2–20 mM, preferably 5–10 mM MgCl$_2$, 0.1–10 mM, preferably 0.5–2.0 mM ATP and 1–50 mM, preferably 5–10 mM dithiothreitol at 1°–37° C., preferably 3°–20° C. for 15 minutes to 72 hours, preferably 2–20 hours. The recombinant plasmid DNA formed by the ligation reaction is introduced into *Escherichia coli* by the transformation method of Cohen, et al. [S. N. Cohen, et al.: Proc. Natl, Acad. Sci. USA 69, 2110 (1972)], if necessary. Isolation of the recombinant plasmid DNA from *Escherichia coli* carrying the DNA is carried out by the method described in Example 1 or the method of Birnboim, et al. [H. C. Birnboim, et al.: Nucleic Acids Res. 7, 1513 (1979)]. Plasmid DNA is digested with 1–10 kinds of restriction endonucleases and the cleavage sites are examined by agarose gel electrophoresis or polyacrylamide gel electrophersis. Further, if necessary, the base sequence of the DNA is determined by the method of Maxam-Gilbert [Proc. Natl. Acad. Sci. 74, 560 (1977)].

The derivative of IFN-γ polypeptide of the present invention is produced by the following method.

That is, *Escherichia coli* K-12 HB101 is transformed with a plasmid such as pGVA-4 and an *Escherichia coli* strain carrying pGVA-4 is selected from the ampicillin resistant (referred to as Ap$^R$ hereinafter) colonies. The *Escherichia coli* strain carrying pGVA-4 is cultured in a medium to produce a derivative of IFN-γ polypeptide in the cultured cells.

As the medium, either a synthetic medium or a natural medium can be used so long as it is suitable for the growth of *Escherichia coli* and the production of the derivative of IFN-γpolypeptide.

As a carbon source, glucose, fructose, lactose, glycerol, mannitol, sorbitol, etc. may be used.

As a nitrogen source, NH$_4$Cl, (NH$_4$)$_2$SO$_4$, casamino acid, yeast extract, polypeptone, meat extract, Bacto-trypton, corn steep liquor, etc. may be used.

In addition, nutrients such as K$_2$HPO$_4$, KH$_2$PO$_4$, NaCl, MgSO$_4$, vitamine B$_1$ and MgCl$_2$ may be used.

Culturing is carried out at pH 5.5–8.5 and at 18°–40° C. with aeration and stirring.

After culturing for 5–90 hours, the derivative of human IFN-γ polypeptide is accumulated in cultured cells. The collected cells are treated with lysozyme, disrupted by repeated freezing and thawing and subjected to centrifugation. The thus obtained supernatant fluid is subjected to extraction according to a conventional method for extraction of polypeptides to recover the polypeptide.

Determination of human IFN-γ is carried out according to the method of Armstrong [J. A. Armstrong, et al.: Appl. Microbiol. 21, 723–725 (1971)].

Certain specific embodiments of the present invention are illustrated by the following examples.

EXAMPLE 1

Construction of plasmid pGBD-1 having BamHI cleavage site downstream from IFN-γ gene:

In this example, 2 μg of plasmid pIFNγ-G4 [3.6 kilobases (referred to as Kb hereinafter)] was dissolved in 50 μl (total volume) of a solution containing 20 mM Tris-HCl (pH 7.5), 10 mM MgCl$_2$, 10 mM dithiothreitol and 50 mM NaCl (referred as "Y-50 buffer solution" hereinafter). Then, 4 units of restriction enzyme PvuII (product of Takara Shuzo Co.; the restriction enzymes hereinafter are all products of Takara Shuzo Co., unless otherwise specified) was added and digestion reaction was carried out at 37° C. for 2 hours. 1 μg of DNA fragment (3.6 Kb) of pIFNγ-G4 was purified by LGT method. 0.1 μg of the DNA fragment and 5 pmoles of 5'-phosphorylated BamHI linker (5'-pCCGGATCCGG-3': product of Collaborative Research, Inc.) were ligated at 4° C. for 18 hours with 2 units of T4 ligase (product of Takara Shuzo Co.; the same shall apply hereinafter) in 20 μl of a buffer solution consisting of 20 mM Tris-HCl (pH 7.6), 10 mM MgCl$_2$, 10 mm dithiothreitol and 0.5 mM ATP (referred to as "T4 ligase buffer solution" hereinafter).

*Escherichia coli* HB101 [Boliver, et al.: GENE 2, 75 (1977)] was transformed using the thus obtained recombinant plasmid DNA by the method of Cohen, et al. [S. N. Cohen, et al.: Proc. Natl. Acad. Sci. USA. 69, 2110 (1972), the method is used for transformation of *Escherichia coli* hereinafter] to obtain an Ap$^R$ colony. Plasmid DNA was isolated from the transformant by the known method [H. C. Birnboim, et al.: Nucleic Acids Res., 7, 1513 (1979), this method is used for isolation of plasmid DNA hereinafter]. The DNA was digested with restriction endonucleases such as BamHI and its structure was analyzed to recognize that recombinant plasmid pGBD-1 wherein BamHI linker was inserted into PvuII site of pIFNγ-G4 was obtained. *Escherichia coli* strain carrying plasmid pGBD-1 has been deposited with the Fermentation Research Institute, Agency of Industrial Science and Technology (referred to as FERM hereinafter) as *Escherichia coli* IGBD-1 (FERM BP-394).

EXAMPLE 2

Construction of recombinant plasmid pGVA-4 coding for 3-Tyr-IFN-γ:

pGBD-1 obtained in Example 1 was treated by the following method to remove the modification of DNA and make SinI cleavage site in the plasmid. *Escherichia coli* GM31 (thr leu dcm his thi ara lac galK, galT, xyl mtl str tonA) [Marinus, et al.: Molec. Gen. Genet. 127, 47–55 (1973)] was transformed with pGBD-1 by a conventional method. A large amount of pGBD-1 was prepared from the thus obtained colonies by a conventional method. 6 μg of the thus obtained pGBD-1 DNA was dissolved in 50 μl of Y-50 buffer solution. 10 units of SinI (product of Bio Tech Co.) was added and digestion reaction was carried out at 37° C. for 3 hours. Then, NaCl was added to a final concentration of 100 mM and 10 units of BamHI was added. Digestion reaction was carried out at 37° C. for 3 hours. About 0.8 μg of DNA fragment of about 850 base pairs (referred to as bp hereinafter) containing the most part of human IFN-γ DNA was obtained from the reaction solution by LGT method.

Separately, 3 μg of pKYP10 prepared by the method described in Japanese Published Unexamined Patent Application No. 110600/83 was dissolved in 40 μl (total volume) of a buffer solution consisting of 20 mM Tris-HCl (pH 7.5), 10 mM MgCl$_2$, 10 mM dithiothreitol and 100 mM NaCl (referred to as "Y-100 buffer solution" hereinafter) and 5 units each of ClaI (product of Boehringer Mannheim GmbH) and BamHI were added. Digestion reaction was carried out at 37° C. for 3 hours. From the reaction solution, about 1.8 μg of DNA fragment of about 4.3 Kb containing tryptophan promoter (P$_{trp}$) was obtained by LGT method.

Mature human IFN-γ polypeptide has the N-terminal structure of Cys-Tyr-Cys-. In order to change the third amino acid (Cys) to Tyr and to furnish an initiation codon (ATG) necessary for expression just before the first Cys, the following DNA linker was synthesized.

Two single chain DNAs of 17-mer and 18-mer were synthesized by a conventional triester method [R. Crea. et al: Proc. Natl. Acad. Sci., 75, 5765 (1978)]. Then, 2 μg each of the 17-mer and 18-mer DNAs were dissolved in 40 μl (total volume) of a solution containing 50 mm Tris-HCl (pH 7.5), 10 mM MgCl$_2$, 5 mM dithiothreitol, 0.1 mM EDTA and 1 mM ATP. 30 units of T4 polynucleotide kinase (product of Takara Shuzo Co.) was added and phosphorylation reaction was carried out at 37° C. for 60 minutes.

0.4 μg of the SinI-BamHI fragment of about 850 bp obtained above and derived from pGBD-1 and 1.0 μg of the ClaI-BamHI fragment of about 4.3 Kb of the expression vector pKYP10 obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

*Escherichia coli* HB101 was transformed using the obtained recombinant plasmid mixture to obtain an Ap$^R$ colony. A plasmid pGSB-6 illustrated in FIG. 2 was isolated from the culture broth of the colony. The structure of pGSB-6 was confirmed by the digestion with EcoRI, ClaI, and BamHI and agarose gel electrophoresis. It was confirmed by the method of Maxam-Gilbert [A. M. Maxam, et al.: Proc. Natl. Acad. Sci., USA 74, 560 (1977)] that the base sequence around ClaI-SinI in the plasmid pGSB-6 is

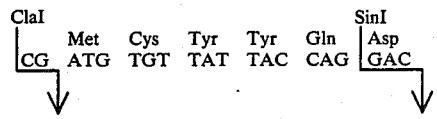

The human IFN-γ polypeptide encoded by pGSB-6 (the derivative is named 3-Tyr-IFN-γ hereinafter) is clearly different from the known human IFN-γ polypeptide in that the third amino acid (Cys) of mature human IFN-γ is replaced with Tyr.

Then, 1 μg of the pGSB-6 was dissolved in 30 μl (total volume) of Y-50 buffer solution and 2 units of ClaI was added. Digestion reaction was carried out at 37° C. for 2 hours. A DNA fragment was recovered by phenol extraction, chloroform extraction and ethanol precipitation. The DNA fragment was dissolved in 30 μl of a solution consisting of 67 mM Tris-HCl (pH 8.8), 6.7 mM MgCl$_2$, 10 mM mercaptoethanol, 6.7 μM EDTA, 16.6 mM (NH$_4$)$_2$SO$_4$, 1 mM dATP, 1 mM dCTP, 1 mM dGTP and 1 mM dTTP and 5 units of T4 DNA polymerase (product of Takara Shuzo Co.) was added, followed by fill-in reaction at 37° C. for 1 hour. A DNA fragment was recovered by phenol extraction, chloroform extraction and ethanol precipitation. 0.1 μg of the DNA fragment was dissolved in 50 μl of T4 ligase buffer solution. 2 units of T4 ligase was added and ligation reaction was carried out at 4° C. for 16 hours.

*Escherichia coli* HB101 was transformed using the thus obtained DNA mixture and plasmid DNA, pGVA-4, was recovered from the formed Ap$^R$ colony. The structure of pGVA-4 was recognized by the cleavage with NruI, BamHI and EcoRI. The base sequence between SD and ATG of pGVA-4 was confirmed by the method of Maxam and Gilbert described above and is illustrated below.

*Escherichia coli* strain carrying plasmid pGVA-4 has been deposited with the FERM as *Escherichia coli* IG-VA-4 (FERM BP-395).

EXAMPLE 3

Construction of recombinant plasmid pGVK-13 coding for 1,3-Ser-IFN-γ:

6 μg of pGBD-1 DNA obtained in Example 1 was dissolved in 50 μl of Y-50 buffer solution. 10 units of SinI (product of Bio Tec Co.) was added and digestion reaction was carried out at 37° C. for 3 hours. Then, NaCl was added to a final concentration of 100 mM and 10 units of BamHI was added. Digestion reaction was carried out at 37° C. for 3 hours. About 0.8 μg of DNA fragment of about 850 bp containing the most part of human IFN-γ DNA was obtained from the reaction solution by LGT method. Separately, 3 μg of pKYP-10 was dissolved in 40 μl (total volume) of Y-100 buffer solution and 5 units each of HindIII and BamHI were added. Digestion reaction was carried out at 37° C. for 3 hours. From the reaction solution, about 1.8 μg of DNA fragment of about 4.3 Kb containing $P_{trp}$ was obtained by LGT method.

Mature human IFN-γ polypeptide has the N-terminal structure of Cys-Tyr-Cys-. In order to change the first and third amino acids (Cys) to Ser and to furnish an initiation codon (ATG) necessary for expression just before the first Ser, the following DNA linker was synthesized.

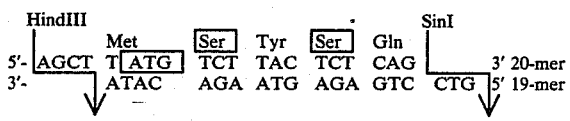

Two single chain DNAs of 20-mer and 19-mer were synthesized by a conventional triester method [R. Crea, et al.: Proc. Natl. Acad. Sci., 75, 5765 (1978)]. Then, 2 μg each of the 20-mer and 19-mer DNAs were dissolved in 40 μl (total volume) of a solution containing 50 mM Tris-HCl (pH 7.5), 10 mM $MgCl_2$, 5 mM dithiothreitol, 0.1 mM EDTA and 1 mM ATP. 30 units of T4 polynucleotide kinase (product of Takara Shuzo Co.) was added and phosphorylation reaction was carried out at 37° C. for 60 minutes.

0.4 μg of the SinI-BamHI fragment of about 850 bp obtained above and derived from pGBD-1 and 1.0 μg of the HindIII-BamHI fragment of about 4.3 Kb of the expression vector pKYP10 obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

Escherichia coli HB101 was transformed using the obtained recombinant plasmid mixture to obtain an $Ap^R$ colony. A plasmid, pGVK-13 illustrated in FIG. 3 was isolated from the culture broth of the colony. The structure of pGVK-13 was confirmed by the digestion with EcoRI, HindIII, ClaI, and BamHI and agarose gel electrophoresis. It was confirmed by the method of Maxam-Gilbert that the base sequence from HindIII site to SinI site in the plasmid pGVK-13 is as follows.

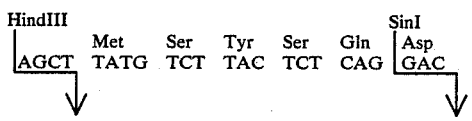

The human IFN-γ polypeptide encoded by pGVK-13 (the derivative is named 1,3-Ser-IFN-γ hereinafter) is clearly different from the known human IFN-γ polypeptide in that the first and third amino acids (Cys) of mature human IFN-γ are replaced with Ser. Escherichia coli strain carrying plasmid pGVK-13 has been deposited with the FERM as Escherichia coli IGVK-13 (FERM BP-432).

EXAMPLE 4

Construction of plasmid pGWC-10 coding for the polypeptide wherein an N-terminal region of human IFN-γ is deleted:

25 μg of pGKA-2 (5.2 Kb) obtained by the method of Reference Example 2 was dissolved in 400 μl of a buffer solution consisting of 20 mM Tris-HCl (pH 7.5), 10 mM $MgCl_2$, 10 mM dithiothreitol and 10 mM NaCl (referred to as "Y-10 buffer solution" hereinafter). 50 units of ClaI (product of Boehringer Mannheim GmbH) was added and digestion reaction was carried out at 37° C. for 3 hours. To 80 μl of the reaction solution containing 5 μg of DNA, were added 12 μl of 10-fold concentrated BAL31 buffer solution [200 mM Tris-HCl (pH 8.1), 1M NaCl, 120 mM $CaCl_2$], 28 μl of water and 0.25 unit of nuclease BAL31 [product of Bethesda Research Laboratories (BRL)] and reaction was carried out at 30° C. for 20 seconds. BAL31 has the activity of exonuclease which digests from the end of a DNA molecule and about 30 base pairs of DNA from ClaI site were digested under the conditions described above. DNA was recovered from the reaction solution by phenol extraction, chloroform extraction and ethanol precipitation. 1.0 μg of the thus recovered pGKA-2 fragment digested with ClaI and BAL31 was dissolved in 20 μl of Y-50 buffer solution. 2 units of PstI was added and digestion reaction was carried out at 37° C. for 2 hours. From the reaction solution, 0.5 μg of DNA fragment of about 4.3 Kb was recovered by LGT method.

Then, 5.0 μg of ATG expression vector pTrS3 (3.8 Kb) was dissolved in 40 μl of Y-50 buffer solution. 10 units of SphI (product of BRL) was added and digestion reaction was carried out at 37° C. for 3 hours. After phenol extraction and chloroform extraction, about 3.0 μg of DNA fragment was recovered by ethanol precipitation. About 3.0 μg of the DNA fragment was dissolved in a solution consisting of 67 mM Tris-HCl (pH 8.3), 6.7 mM $MgCl_2$, 10 mM mercaptoethanol, 6.7 μM EDTA and 16.6 mM $(NH_4)_2SO_4$ and 1 mM each of dATP, dTTP, dCTP and dGTP were added. Further, 6 units of T4 DNA polymerase (product of Takara Shuzo Co., the same shall apply hereinafter) was added and reaction was carried out at 37° C. for 1 hour to digest the protruding end. After phenol extraction and chloroform extraction, 1.0 μg of DNA fragment was recovered by ethanol precipitation. 1.0 μg of the DNA fragment was dissolved in 20 μl (total volume) of Y-50 buffer solution. 2 units of PstI was added and digestion reaction was carried out at 37° C. for 3 hours. From the reaction solution, 0.5 μg of DNA fragment of about 880 bp containing $P_{trp}$ was recovered by LGT method.

0.5 μg of ClaI-PstI fragment (about 4.3 Kb) of pGKA2 obtained above and 0.5 μg of PTrS3-SphI-T4 polymerase-PstI fragment (880 bp) obtained above were dissolved in 10 μl (total volume) of T4 ligase buffer solution. 0.3 unit of T4 DNA ligase was added and ligation reaction was carried out at 4° C. for 18 hours.

Figure 5:
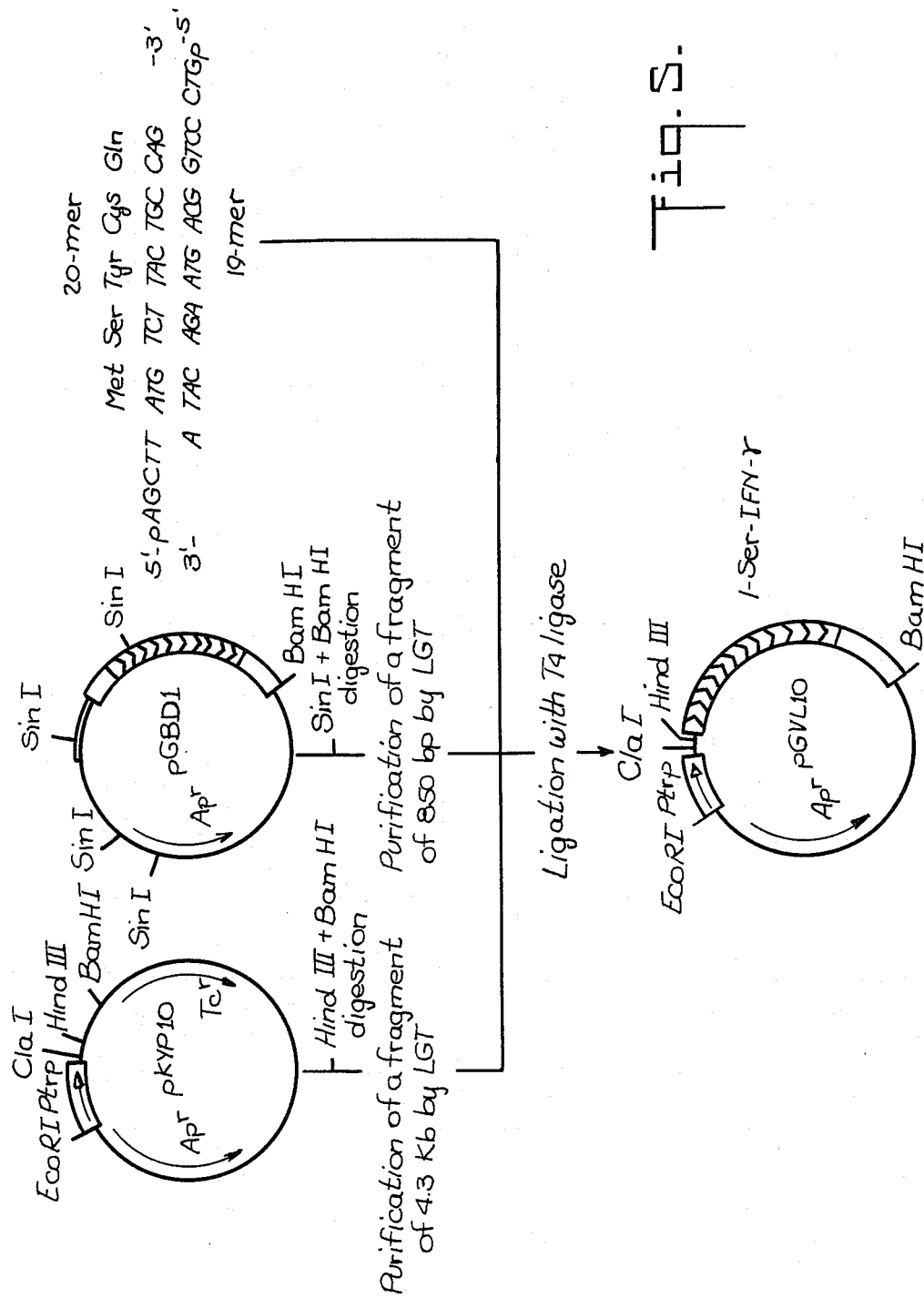
FIG. 5 is the process for constructing pGVL-10.

Escherichia coli HB101 was transformed using the thus obtained recombinant plasmid mixture and plasmid DNA was recovered from the Ap$^R$ colony formed to obtain pGWC-10 illustrated in Fig. 5. The structure of pGWC-10 was recognized by the digestion with EcoRI, ClaI and BamHI and agarose gel electrophoresis. It was confirmed by the method of Maxam and Gilbert that the sequence around N-terminal of human IFN-γ structure gene in pGWC-10 was as follows.

```
  Met  Val  Gln  Glu  Ala  Glu
 -ATG  GTA  CAA  GAA  GCA  GAA
```

It was also confirmed that seven amino acids from the N-terminal amino acid (Cys) to the seventh amino acid (Tyr) of the mature human IFN-γ polypeptide were deleted and that the human IFN-γ polypeptide derivative was started with the eighth amino acid (Val) [the derivative is named IFN-γ (Δ1-7)]. Escherichia coli strain carrying plasmid pGWC-10 has been deposited with the FERM as Escherichia coli IGWC-10 (FERM BP-397).

EXAMPLE 5

Production of IFN-γ derivatives by Escherichia coli strains carrying pGBD-1, pGVA-4, pGVK-13 and pGWC-10:

Escherichia coli HB101 strains carrying recombinant plasmids pGBD-1, pGVA-4, pGVK-13 and pGWC-10 obtained in Examples 1-4, which are named IGBD-1, IGVA-4, IGVK-13 and IGWC-10 respectively, were cultured at 37° C. for 18 hours in LG medium (10 g of trypton, 5 g of yeast extract, 5 g of NaCl, 2 g of glucose, 1 l of water, adjusted to pH 7.0 with NaOH). 0.2 ml of the culture broth was inoculated into 10 ml of MCG medium (0.6% Na$_2$HPO$_4$, 0.3% KH$_2$PO$_4$, 0.5% NaCl, 0.1% NH$_4$Cl, 0.5% glucose, 0.5% casamino acid, 1 mM MgSO$_4$, 4 μg/ml vitamine B$_1$, pH 7.2) and culturing was carried out at 30° C for 4 hours. Then, 10 μg/ml indolacrylic acid (referred to as IAA hereinafter) which is an inducer of tryptophan operon was added and culturing was continued for 4 hours. The culture broth was centrifuged at 8,000 rpm for 10 minutes and the cells harvested were washed with a buffer solution containing 30 mM NaCl and 30 mM Tris-HCl (pH 7.5). Washed cells were suspended in 1 ml of the buffer solution described above and 5 μl of a solution containing 200 μg of lysozyme and 0.25M EDTA (ethylenediamine tetraacetic acid) was added. The mixture was allowed to stand at 0° C. for 30 minutes and freezing and thawing were repeated three times to disrupt the cells. The disrupted cells were centrifuged at 15,000 rpm for 30 minutes to obtain a supernatant fluid. The amount of interferon in the supernatant was determined according to the mothod of Armstrong [J. A. Armstrong, et al.: Appl. Microbiol. 21, 723–725 (1971)], wherein Sindvis virus was used as the virus and FL cells derived from human amnion cells were used as the animal cells. The results are shown in Table 2.

TABLE 2

| Strains | Plasmid | Product encoded by the plasmid | IFN-γ (units/ml) |
|---|---|---|---|
| IGBD-1 | pGBD-1 | IFN-γ | trace |
| IGVA-4 | pGVA-4 | 3-Tyr—IFN-γ | 9 × 10$^4$ |
| IGVK-13 | pGVK-13 | 1,3-Ser—IFN-γ | 2 × 10$^5$ |
| IGWC-10 | pGWC-10 | IFN-γ(Δ1–7) | 5 × 10$^4$ |

TABLE 2-continued

| Strains | Plasmid | Product encoded by the plasmid | IFN-γ (units/ml) |
|---|---|---|---|
| IGKA-2 | pGKA-2 | IFN-γ | 2 × 10$^4$ |

IGKA-2 is a strain carrying plasmid pGKA-2 coding for IFN-γ.

EXAMPLE 6

Construction of recombinant plasmid pGVL10 coding for 1-Ser-IFN-γ:

6 μg of pGBD1 DNA obtained in Example 1 was dissolved in 50 μl of Y-50 buffer solution. 10 units of SinI was added and digestion reaction was carried out at 37° C. for 3 hours. Then, NaCl was added to a final concentration of 100 mM and 10 units of BamHI was added. Digestion reaction was carried out at 37° C. for 3 hours. About 0.8 μg of DNA fragment of about 850 bp containing the most part of human IFN-γ DNA was obtained from the reaction solution by LGT method.

Separately, 3 μg of pKYP10 DNA prepared by the method described in Japanese Published Unexamined Patent Application No. 110600/83 was dissolved in 40 μl (total volume) of Y-50 buffer solution and 5 units each of HindIII and BamHI were added. Digestion reaction was carried out at 37° C. for 3 hours. From the reaction solution, about 1.8 μg of DNA fragment of about 4.3 Kb containing tryptophan promoter (P$_{trp}$) was obtained by LGT method.

Mature human IFN-γ polypeptide has the N-terminal structure of Cys-Tyr-Cys-. In order to change the first Cys to Ser and to furnish an initiation codon (ATG) necessary for expression just before the first Ser, the following DNA linker was synthesized.

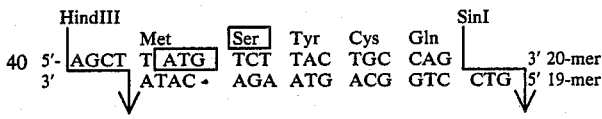

Two single chain DNAs of 20-mer and 19-mer were synthesized by a conventional triester method [R. Crea, et al.: Proc. Natl. Acad. Sci., USA, 75, 5765 (1978)]. Then, 2 μg each of the 20-mer and 19-mer DNAs were dissolved in 40 μl (total volume) of a solution containing 50 mM Tris-HCl (pH 7.5), 10 mM MgCl$_2$, 5 mM dithiothreitol, 0.1 mM EDTA and 1 mM ATP. 30 units of T4 polynucleotide kinase was added and phosphorylation reaction was carried out at 37° C. for 60 minutes.

0.5 μg of the SinI-BamHI fragment of about 850 bp obtained above and derived from pGBD-1 and 1.0 μg of the HindIII-BamHI fragment of about 4.3 Kb of the expression vector pKYP-10 were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

Escherichia coli HB101 was transformed using the obtained recombinant plasmid mixture to obtain an Ap$^R$ colony. A plasmid, pGVL10 illustrated in FIG. 5 was isolated from the culture broth of the colony. The structure of pGVL10 was confirmed by the digestion with EcoRI, ClaI, HindIII and BamHI and agarose gel elecrophoresis. It was confirmed by the method of Maxam-Gilbert [A. M. Maxam, et al.: Proc, Natl, Acad, Sci.

USA, 74, 560 (1977)] that the base sequence from HindIII site to SinI site in the plasmid pGVL10 is as follows.

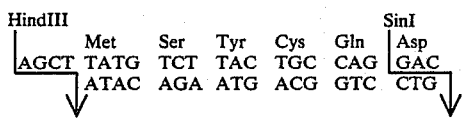

The human IFN-γ polypeptide encoded by pGVL10 (the derivative is named 1-Ser-IFN-γ hereinafter) is clearly different from the known human IFN-γ polypeptide in that the first Cys of mature human IFN-γ is replaced with Ser. *Escherichia coli* strain carrying plasmid pGVL10 has been deposited with the FERM as *Escherichia coli* IGVL10 (FERM BP-544).

EXAMPLE 7

Construction of recombinant plasmid pGVM101 coding for 3-Ser-IFN-γ:

6 μg of pGBD1 DNA obtained in Example 1 was dissolved in 50 μl pf Y-50 buffer solution. 10 units of Sin I was added and digestion reaction was carried out at 37° C. for 3 hours. Then, NaCl was added to a final concentration of 100 mM and 10 units of BamHI was added. Digestion reaction was carried out at 37° C. for 3 hours. About 0.8 μg of DNA fragment of about 850 bp containing the most part of human IFN-γ DNA was obtained from the reaction solution by LGT method.

Separately, 3 μg of pKYP10 DNA prepaed by the method described in Japanese Published Unexamined Patent Application No. 110600/83 was dissolved in 40 μl (total volume) of Y-50 buffer solution and 5 units each of HindIII and BamHI were added. Digestion reaction was carried out at 37° C. for 3 hours. From the reaction solution, about 1.8 μg of DNA fragment of about 4.3 Kb containing tryptophan promoter ($P_{trp}$) was obtained by LGT method.

Mature human IFN-γ polypeptide has the N-terminal structure of Cys-Tyr-Cys-. In order to change the third amino acid (Cys) to Ser and to furnish an initiation codon (ATG) necessary for expression just before the first Cys, the following DNA linker was synthesized.

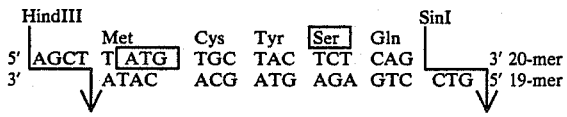

Two single chain DNAs of 20-mer and 19-mer were synthesized by a conventional triester method. Then, 2 μg each of the 20-mer and 19-mer DNAs were dissolved in 40 μl (total volume) of a solution containing 50 mM Tris-HCl (pH 7.5), 10 mM $MgCl_2$, 5 mM dithiothreitol, 0.1 mM EDTA and 1 mM ATP. 30 units of T4 polynucleotide kinase was added and phosphorylation reaction was carried out at 37° C. for 60 minutes.

0.5 μg of the SinI-BamHI fragment of about 850 bp obtained above and derived from pGBD1 and 1.0 μg of the HindIII-BamHI fragment of about 4.3 Kb of the expression vector pKYP10 were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

Figure 6:
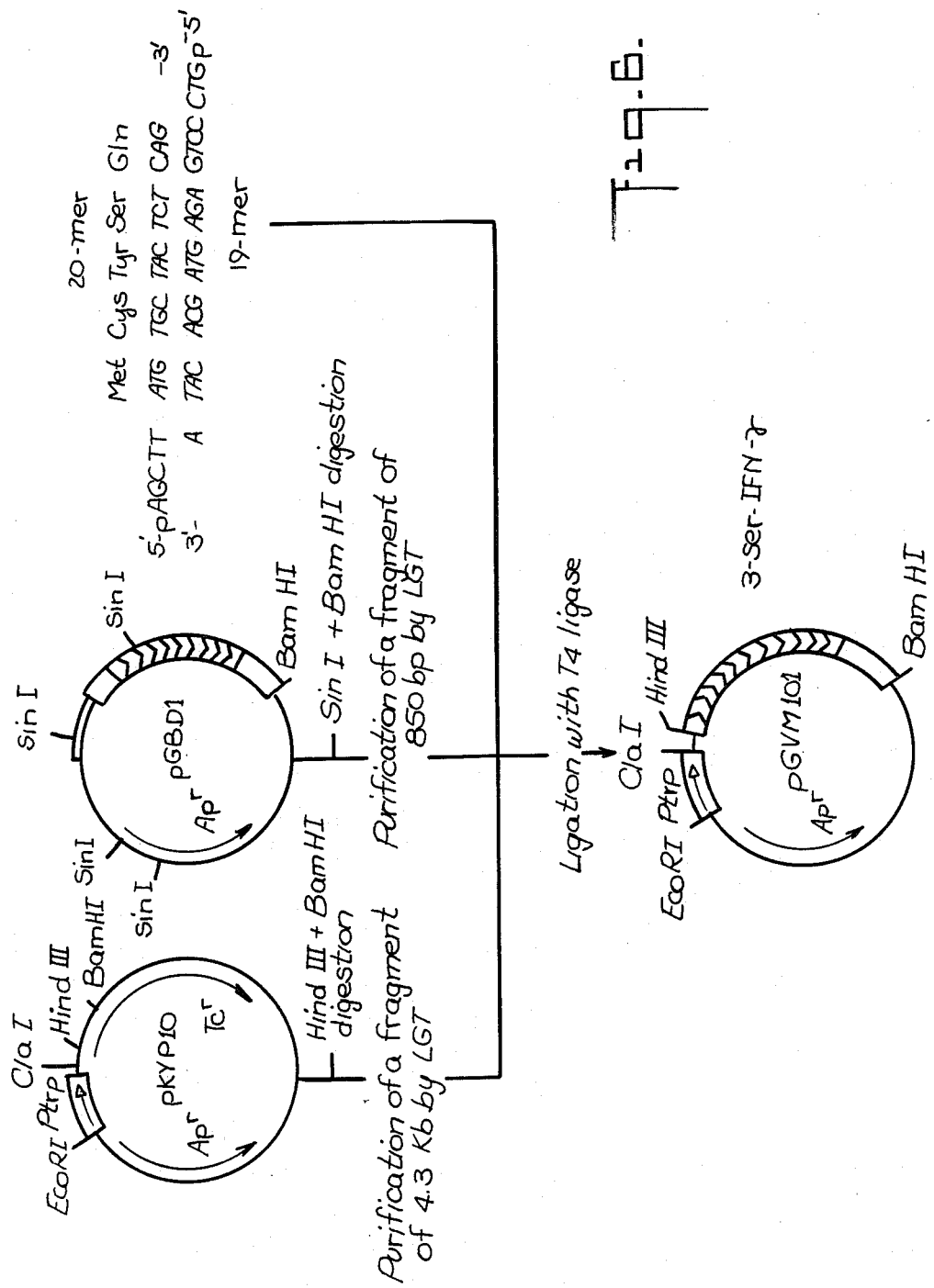
FIG. 6 is the flow sheet for constructing pGVM101.

*Escherichia coli* HB101 was transformed using the obtained recombinant plasmid mixture to obtain an $Ap^R$ colony. A plasmid, pGVM101 illustrated in FIG. 6 was isolated from the culture broth of the colony. The structure of pGVM101 was confirmed by the digestion with EcoRI, ClaI, HindIII, and BamHI and agarose gel electrophoresis. It was confirmed by the method of Maxam-Gilbert that the base sequence from HindIII site to SinI site in the plasmid pGVM101 is as follows.

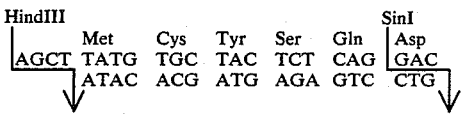

The human IFN-γ polypeptide encoded by pGVM101 (the derivative is named 3-Ser-IFN-γ hereinafter) is clearly different from the known human IFN-γ polypeptide in that the third amino acid (Cys) of mature human IFN-γ is replaced with Ser. *Escherichia coli* strain carrying plasmid pGVM101 has been deposited with the FERM as *Escherichia coli* IGVM101 (FERM BP-545).

EXAMPLE 8

Construction of plasmid pGWE4 coding for the polypeptide wherein an N-terminal region of human IFN-γ is deleted:

25 μg of pGKA2 (5.2 Kb) obtained by the method of Reference Example 2 was dissolved in 400 μl of Y-10 buffer solution. 50 units of ClaI was added and digestion reaction was carried out at 37° C. for 3 hours. To 80 μl of the reaction solution containing 5 μg of DNA, were added 12 μl of 10-fold concentrated BAL31 buffer solution, 28 μl of water and 0.25 unit of nuclease BAL31 and reaction was carried out at 30° C. for 10 seconds. BAL31 has the activity of exonuclease which digests from the end of a DNA molecule and about 20 base pairs of DNA from ClaI side were digested under the conditions described above. DNA was recovered from the reaction solution by phenol extraction, chloroform extraction and ethanol precipitation. 1.0 μg of the thus recovered pGKA2 fragment digested with ClaI and BAL31 was dissolved in 20 μl of Y-50 buffer solution. 2 units of PstI was added and digestion reaction was carried out at 37° C. for 2 hours. From the reaction solution, 0.5 μg of DNA fragment of about 4.3 Kb was recovered by LGT method.

Then, 5.0 μg of ATG expression vector pTrS3 (3.8 Kb) was dissolved in 40 μl of Y-50 buffer solution. 10 units of SphI was added and digestion reaction was carried out at 37° C. for 3 hours. After phenol extraction and chloroform extraction, about 3.0 μg of DNA fragment was recovered by ethanol precipitation. About 3.0 μg of the DNA fragment was dissolved in a solution consisting of 67 mM Tris-HCl (pH 8.3), 6.7 mM $MgCl_2$, 10 mM mercaptoethanol, 6.7 μM EDTA and 16.6 mM $(NH_4)_2SO_4$ and 1 mM each of dATP, dTTP, dCTP and dGTP were added. Further, 6 units of T4 DNA polymerase was added and reaction was carried out at 37° C. for 1 hour to digest the protruding end. After phenol extraction and chloroform extraction, 1.0 μg of DNA fragment was recovered by ethanol precipitation. 1.0 μg of the DNA fragment was dissolved in 20 μl (total volume) of Y-50 buffer solution. 2 units of PstI was added and digestion reaction was carried out at 37° C. for 3 hours. From the reaction solution, 0.5 μg of DNA fragment of about 880 bp containing P$_{trp}$ was recovered by LGT method.

0.5 μg of ClaI-PstI fragment (about 4.3 Kb) of pGKA2 obtained above and 0.5 μg of pTrS3-SphI-T4 polymerase-PstI fragment (880 bp) obtained above were dissolved in 10 μl (total volume) of T4 ligase buffer solution. 0.3 unit of T4 DNA ligase was added and ligation reaction was carried out at 4° C. for 18 hours.

Figure 7:
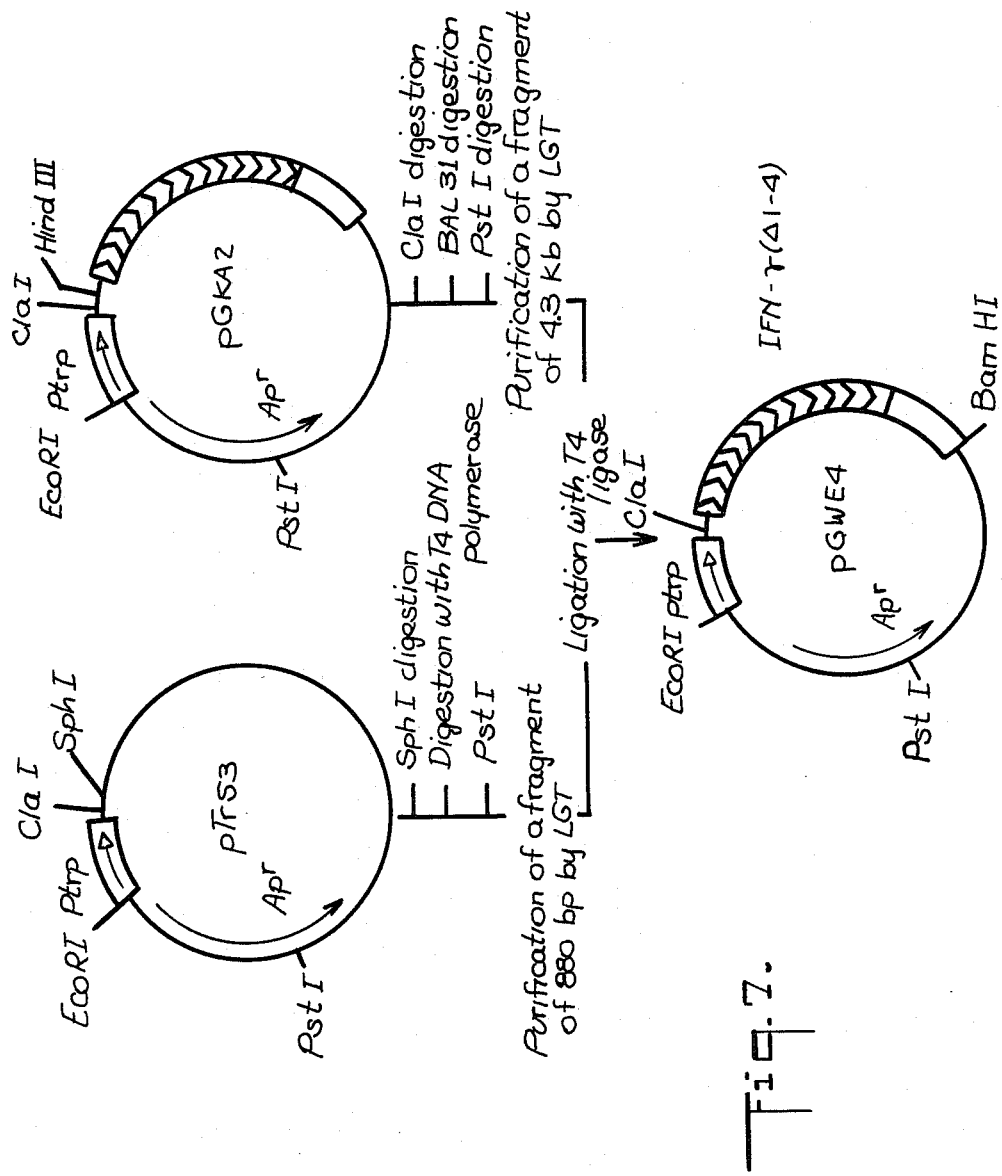
FIG. 7 is the flow sheet for constructing pGWE4.

*Escherichia coli* HB101 was transformed using the thus obtained recombinant plasmid mixture and plasmid DNA was recovered from the Ap$^R$ colony formed to obtain pGWE4 illustrated in FIG. 7. The structure of pGWE4 was recognized by the digestion with EcoRI, ClaI and BamHI and agarose gel electrophoresis. It was confirmed by the method of Maxam and Gilbert that sequence around N-terminal of human IFN-γ structure gene in pGWE4 was as follows.

```
    Met  Asp  Pro  Tyr  Val  Gln
   -ATG  GAC  CCA  TAT  GTA  CAA
```

It was also confirmed that four amino acids from the N-terminal amino acid (Cys) to the fourth amino acid (Gln) of the mature human IFN-γ polypeptide were deleted and that the human IFN-γ polypeptide derivative was started with the fifth amino acid (Asp) [the derivative is named IFN-γ(Δ1-4)]. *Escherichia coli* strain carrying plasmid pGWE4 has been deposited with the FERM as *Escherichia coli* IGWE4 (FERM BP-546).

EXAMPLE 9

Production of IFN-γ derivatives by *Escherichia coli* strains carrying pGVL10, pGVM101 and pGWE4:

*Escherichia coli* HB101 strains carrying recombinant plasmids pGVL10, pGVM101 and pGWE4 obtained in Examples 6–8, which are named IGVL10, IGVM101, and IGWE4 respectively, were cultured at 37° C. for 18 hours in LG medium. 0.2 ml of the culture broth was inoculated into 10 ml of MCG medium and culturing was carried out at 30° C. for 4 hours. Then 10 μg/ml IAA was added and culturing was continued for 4 hours. The culture broth was centrifuged at 8,000 rpm for 10 minutes and the cells harvested were washed with a buffer solution containing 30 mM NaCl and 30 mM Tris-HCl (pH 7.5). Washed cells were suspended in 1 ml of the buffer solution described above and 5 μl of a solution containing 200 μg of lysozyme and 0.25M EDTA was added. The mixture was centrifuged for 30 minutes to obtain a supernatant fluid. The amount of interferon in the supernatant was determined according to the method of Armstrong, wherein Sindvis virus was used as the virus and FL cells derived from human amnion cells were used as the animal cells. The results are shown in Table 3.

TABLE 3

| Strains | Plasmid | Product encoded by the plasmid | IFN-γ (units/ml) |
|---------|---------|-------------------------------|------------------|
| IGBD1   | pGBD1   | IFN-γ                         | trace            |
| IGVL10  | pGVL10  | 1-Ser—IFN-γ                   | 8 × 10$^4$       |
| IGVM101 | pGVM101 | 3-Ser—IFN-γ                   | 3 × 10$^5$       |
| IGWE4   | pGWE4   | IFN-γ(Δ1-4)                   | 2 × 10$^5$       |
| IGKA2   | pGKA2   | IFN-γ                         | 2 × 10$^4$       |

IGKA2 is a strain carrying plasmid pGKA2 coding for IFN-γ.

REFERENCE EXAMPLE 1

Insertion of human IFN-γ DNA into the expression vector pKYP-11:

In this example, 6 μg of plasmid pIFNγ-G4 (3.6 Kb) was dissolved in 50 μl (total volume) of a solution containing 20 mM Tris-HCl (pH 7.5), 10 mM MgCl$_2$, 10 mM dithiothreitol and 50 mM NaCl. Then, 12 units each of restriction enzymes PvuII and HindIII were added and digestion reaction was carried out at 37° C. for 4 hours. The reaction solution was heated at 65° C. for 7 minutes to inactivate the enzymes and subjected to purification by LGT method to obtain 1.2 μg of a DNA fragment of 1.3 Kb containing human IFN-γ DNA.

Separately, 4 μg of pKYP-11 was dissolved in 40 μl (total volume) of a solution containing 20 mM Tris-HCl (pH 7.5), 10 mM MgCl$_2$, 10 mM dithiothreitol and 50 mM NaCl. 8 units of BamHI was added and digestion reaction was carried out at 37° C. for 3 hours. The reaction solution was heated at 65° C. for 5 minutes to inactivate the enzyme. Thereafter, 30 μM each of dATP, dCTP, dGTP and dTTP were added and 8 units of *Escherichia coli* DNA polymerase I (Klenow fragment, product of New England Biolabs, 1 μl) was added. Fill-in reaction was carried out at 15° C. for 1 hour and the reaction solution was heated at 68° C. for 15 minutes to inactivate DNA polymerase I. 10 units of HindIII was added and digestion reaction was carried out at 37° C. for 3 hours, followed by heating at 65° C. for 5 minutes to inactivate HindIII. The digestion reaction solution of the plasmid pKYP-11 was subjected to purification by LGT method to obtain about 2.5 μg of a DNA fragment of about 4.7 Kb containing p$_{trp}$.

Then, 0.5 μg of the DNA fragment of 1.3 Kb containing human IFN-γ DNA and 1.0 μg of the DNA fragment of about 4.7 Kb containing P$_{trp}$, which was obtained from the plasmid pKYP-11, were dissolved in 20 μl of a solution containing 20 mM Tris-HCl (pH 7.5), 6 mM MgCl$_2$, 5 mM dithiothreitol and 500 μM ATP, and 4 units of T4 DNA ligase (product of New England Biolabs) was added. Ligation reaction was carried out at 4° C. for 18 hours, and *Escherichia coli* HB101 was transformed with the obtained recombinant plasmid mixture by conventional technique to obtain an Ap$^R$ colony. A plasmid, pGC-7 was separated from the culture broth of the colony. The structure of pGC-7 was confirmed by the digestion with HindIII, BamHI, HpaI, SalI, EcoRI and ClaI and agarose gel electrophoresis. *Escherichia coli* strain containing pGC-7 has been deposited with the FERM as *Escherichia coli* IGC-7 (FERM P-6814, FERM BP-497).

REFERENCE EXAMPLE 2

Construction of recombinant plasmid pGKA-2:

In this example, 6 μg of the pGC-7 DNA obtained in Reference Example 1 was dissolved in 59 μl (total volume) of a solution containing 20 mM Tris-HCl (pH 7.5), 10 mM MgCl$_2$, 10 mM dithiothreitol and 10 mM NaCl, and 12 units of BstNI (product of New England Biolabs) was added. Reaction was carried out at 60° C. for 3 hours, and the reaction solution was heated at 65° C. for 5 minutes to inactivate BstNI. Then, 150 mM NaCl and 8 units of SalI were added and digestion reaction was carried out at 37° C. for 3 hours. The reaction solution was again heated at 65° C. for 5 minutes to inactivate SalI and subjected to purification by LGT method to obtain about 0.8 μg of a DNA fragment of about 1,125 bp containing the most part of the human IFN-γ DNA.

Separately, 3 μg of pKYP-10 was dissolved in 40 μl (total volume) of a solution containing 20 mM Tris-HCl (pH 7.5), 10 mM MgCl$_2$, 10 mM dithiothreitol and 100 mM NaCl. 6 units each of HindIII and SalI were added and digestion reaction was carried out at 37° C. for 3 hours. The reaction solution was heated at 65° C. for 5 minutes to inactivate HindIII and SalI and subjected to purification by LGT method to obtain about 1.8 μg of a DNA fragment of about 4.1 Kb containing P$_{trp}$.

The N-terminal amino acid of the mature human IFN-γ polypeptide is Cys. In order to express mature IFN-γ DNA, it is necessary to furnish an initiation codon (ATG) just before the 5'-terminal codon TGT (Cys) and further to adjust the length between SD-sequence downstream from Ptrp and ATG to a suitable length of 6–18 bp. Therefore, the following DNA linker was synthesized.

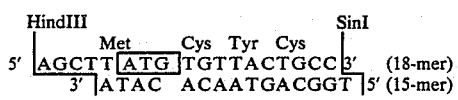

Two single chain DNAs of 18-mer and 15-mer were synthesized by a conventional triester method [R. Crea, et al.: Proc. Natl. Acad. Sci., USA 75, 5765 (1978)]. Then, 2 μg each of the 18-mer and 15-mer DNAs were dissolved in 20 μl (total volume) of a solution containing 50 mM Tris-HCl (pH 7.5), 10 mM MgCl$_2$, 5 mM dithiothreitol, 0.1 mM EDTA and 1 mM ATP. 30 units of T4 polynucleotide kinase (product of Boehringer Mannheim GmbH) was added and phosphorylation reaction was carried out at 37° C. for 60 minutes.

Then, 2 μg each of phosphorylated 18-mer and 15-mer DNAs were mixed and the mixture was heated at 70° C. for 5 minutes and allowed to stand at room temperature for annealing to obtain the DNA linker having the structure given above.

0.4 μg of the BstNI-SalI fragment of 1,125 bp obtained above and derived from pGC-7 and 1.0 μg of the DNA fragment of 4.1 Kb obtained by digestion of the expression vector pKYP-10 with HindIII and SalI were dissolved in 25 μl (total volume) of a solution containing 20 mM Tris-HCl (pH 7.5), 6 mM MgCl$_2$, 5 mM dithiothreitol and 500 μM ATP. About 0.1 μg of the DNA linker mentioned above was added to the mixture, followed by addition of 6 units of T4 DNA ligase. Ligation reaction was carried out at 4° C. for 17 hours. *Escherichia coli* HB101 was transformed using the obtained recombinant plasmid mixture by conventional technique to obtain an Ap$^R$ colony. A plasmid, pGKA-2 illustrated in FIG. 5 was isolated from the culture broth of the colony. The structure of pGKA-2 was confirmed by the digestion with EcoRI, ClaI, HindIII, BstNI and SalI and agarose gel electrophoresis. It was confirmed by the method of Maxam-Gilbert that the base sequence from the SD-sequence (AAGG) to the initiation codon (ATG) in the plasmid pGKA-2 was "AAGGGTATC-GATAAGCTTATG".

*Escherichia coli* strain containing pGKA-2 has been deposited with the FERM as *Escherichia coli* IGKA-2 (FERM P-6798, FERM BP-496).

What is claimed is:

1. A derivative of human interferon-γ polypeptide which is encoded by a recombinant plasmid selected from the group consisting of pGVA-4, pGVK-13, pGWC-10, pGVL-10, pGVM-101 and pGWE-4 which are respectively carried by *Escherichia coli* FERM BP-395, 432, 397, 544, 545 and 546.

* * * * *

UNITED STATES PATENT AND TRADEMARK OFFICE
CERTIFICATE OF CORRECTION

PATENT NO. : 4,758,656

DATED : July 19, 1988

INVENTOR(S) : SEIGA ITOH, ET AL.

It is certified that error appears in the above-identified patent and that said Letters Patent is hereby corrected as shown below:

Column 4, line 48, "IFN-65" should read --IFN-γ--.

Column 9, lines 30-32, that portion of the sequence reading:

```
        "      Met      "
               T ATG
               ATAC
``` should read:

```
               Met
        --   T ATG     --
               ATAC
```

Column 9, lines 61-65, that portion of the sequence reading:

```
        "      Met      "
               TATG
``` should read:

```
        --     Met     --
               TATG
```

UNITED STATES PATENT AND TRADEMARK OFFICE
CERTIFICATE OF CORRECTION

PATENT NO. : 4,758,656

DATED : July 19, 1988

INVENTOR(S) : SEIGA ITOH, ET AL.

It is certified that error appears in the above-identified patent and that said Letters Patent is hereby corrected as shown below:

Column 12, lines 39-41, that portion of the sequence reading:

"      Met      "
     T[ATG]
     ATAC should read:

Met
--  T[ATG]  --
     ATAC

Column 13, lines 6-8, that portion of the sequence reading:

"      Met      "
     TATG
     ATAC should read:

Met
--  TATG  --
     ATAC

UNITED STATES PATENT AND TRADEMARK OFFICE
CERTIFICATE OF CORRECTION

PATENT NO. : 4,758,656
DATED : July 19, 1988
INVENTOR(S) : SEIGA ITOH, ET AL.

Page 3 of 4

It is certified that error appears in the above-identified patent and that said Letters Patent is hereby corrected as shown below:

Column 13, lines 46-48, that portion of the sequence reading:

```
            "     Met         "
                T ATG
                  ATAC
``` should read:

```
              Met
         --  T ATG  --
              ATAC
```

Column 14, lines 11-13, that portion of the sequence reading:

```
            "     Met         "
                  TATG
                  ATAC
``` should read:

```
              Met
         --   TATG  --
              ATAC
```

UNITED STATES PATENT AND TRADEMARK OFFICE
CERTIFICATE OF CORRECTION

PATENT NO. : 4,758,656

DATED : July 19, 1988

INVENTOR(S) : SEIGA ITOH, ET AL.

It is certified that error appears in the above-identified patent and that said Letters Patent is hereby corrected as shown below:

Column 17, lines 20-25, the sequence reading:

```
"  HindIII                    SinI           "
         MetCysTyrCys
    5' AGCTT ATG TGTTACTGCC 3'     (18 mer)
       3' ATAC   ACAATGACGGT  5'   (15 mer)
``` should read:

```
       HindIII              BstNI
            MetCysTyrCys
  --  5' AGCTT ATG TGTTACTGCC 3'   (18-mer)  --.
         3' ATACACAATGACGGT 5'     (15-mer)
```

Signed and Sealed this

Third Day of January, 1989

Attest:

DONALD J. QUIGG

Attesting Officer

Commissioner of Patents and Trademarks